United States Patent
Forrer

(10) Patent No.: US 8,408,045 B2
(45) Date of Patent: Apr. 2, 2013

(54) MEASUREMENT INSTRUMENT FOR DENSITY DETERMINATION

(75) Inventor: Christian Forrer, Elsau (CH)

(73) Assignee: Mettler-Toledo AG, Greifensee (CH)

( * ) Notice: Subject to any disclaimer, the term of this patent is extended or adjusted under 35 U.S.C. 154(b) by 370 days.

(21) Appl. No.: 12/823,395

(22) Filed: Jun. 25, 2010

(65) Prior Publication Data

US 2011/0000321 A1    Jan. 6, 2011

(30) Foreign Application Priority Data

Jul. 1, 2009    (DE) .......................... 10 2009 031 471

(51) Int. Cl.
  *G01N 9/00*    (2006.01)
  *G01N 9/32*    (2006.01)
  *G01N 1/20*    (2006.01)
(52) U.S. Cl. ...................... 73/32 A; 73/32 R; 73/863.71
(58) Field of Classification Search .................. 73/32 R
  See application file for complete search history.

(56) References Cited

U.S. PATENT DOCUMENTS

| | | | | |
|---|---|---|---|---|
| 3,187,584 A | * | 6/1965 | Hudson ........................... | 73/434 |
| 3,902,365 A | * | 9/1975 | Knauth ...................... | 73/861.03 |
| 5,423,750 A | * | 6/1995 | Spiller ............................ | 604/80 |
| 6,029,501 A | * | 2/2000 | Nishino et al. ................. | 73/32 A |

FOREIGN PATENT DOCUMENTS

| | | | |
|---|---|---|---|
| DE | 2757603 C2 | | 1/1980 |
| DE | 8306730 | * | 6/1983 |
| DE | G8306730.2 U1 | | 7/1983 |
| DE | 3308289 C1 | * | 3/1984 |
| DE | 102005044929 B3 | | 6/2007 |
| GB | 2187286 A | * | 9/1987 |
| JP | 07102058 A | * | 4/1995 |

OTHER PUBLICATIONS

Ito et al., JP 07102058 A, Derwent Abstract (1995-183035).*
Bopp et al., DE 8306730, Machine translation downloaded Aug. 1, 2012.*

* cited by examiner

*Primary Examiner* — Peter Macchiarolo
*Assistant Examiner* — Natalie Huls
(74) *Attorney, Agent, or Firm* — Standley Law Group LLP

(57) ABSTRACT

An instrument for measuring density, with a housing (1) and a measurement cell (2) arranged therein. The housing has an inlet opening and an outlet opening for a fluid sample, with a first adapter (12) for connecting the inlet opening to a sample reservoir (14), with a second adapter (11), for connecting the outlet opening to a waste container (15), and with an adapter housing (13), which is attached to the housing. The adapter housing comprises a feed-through for the first and second adapters, characterized in that the adapter housing is designed in one piece, and the adapters can each be affixed in the adapter housing first fastening means without tools.

13 Claims, 3 Drawing Sheets

MEASUREMENT INSTRUMENT FOR DENSITY DETERMINATION

CROSS-REFERENCE TO RELATED APPLICATIONS

This application is entitled to, and claims benefit of, a right of priority under 35 USC §119 from German patent application 10 2009 031471.7, which was filed 1 Jul. 2009. The content of the German application is incorporated by reference as if fully recited herein.

TECHNICAL FIELD

The invention relates to a measurement instrument for density determination having a one-piece adapter housing.

BACKGROUND OF THE ART

A method of density determination includes the introduction of a fluid sample, i.e., liquid and/or gaseous, into a U-shaped measurement cell, e.g., a glass tube capable of vibration. The fluid-filled measurement cell is excited to undamped vibration or oscillation. The density of the sample can be determined on the basis of the change in frequency and the period of the oscillation in comparison with a measurement cell filled with a standard sample. Devices for density measurement that operate by this method are known as flexural resonators.

When loading the measurement cell with a sample, it should be noted that this is done with a predefined quantity or a predefined volume of the sample and with as few bubbles as possible. Manual loading using a suitable pipette or syringe is suggested as the simplest option for filling the cell. However, this is time-consuming, so that for serial measurements in particular, the U-shaped measurement cell is connected to a pump and used as a flow-through cell and/or a sample is added and the inlet line and the outlet line are closed off by valves.

Especially in the case of laboratory instruments in which the U-shaped measurement cell is installed in a housing in a vibration-capable manner, there is the difficulty of connecting the measurement cell to a sample reservoir with a fluid-tight connection without damaging or destroying the measurement cell, which is often made of glass. Furthermore, the measurement results may be impaired because the connections of the measurement cell are also vibrating in a measurement.

Known measurement instruments have a complex adapter housing that is complicated to manufacture and have adapters which often include metal parts for manual and/or automatic loading. Metal parts in particular have the disadvantage that they cannot ensure the required thermal insulation of the measurement cell, an attempt being made to partially compensate same by mathematical correction factors or correction functions. Furthermore, the assembly and connection of the measurement cell to a sample reservoir is complex and may result in damage to the measurement cell. Furthermore, the adapters and the adapter housing also oscillate during a measurement, so that these components may compromise the measurement result on the one hand and on the other hand may be damaged or destroyed by the oscillation.

The object is thus to provide a measurement instrument for density determination using a thermally insulated measurement cell and an improved user-friendly approach for connecting the measurement cell.

SUMMARY

This object is achieved by a measurement instrument for density determination using a measurement cell situated in a housing, which comprises an inlet opening and an outlet opening for a fluid sample. In addition, the measurement instrument comprises a first adapter for connecting the inlet opening to a sample reservoir, a second adapter for connecting the outlet opening to a waste container, and an adapter housing. The adapter housing is attached to the housing and comprises a feed-through for each of the first and second adapters. The adapter housing is designed in one piece, e.g. monolithically, and the adapters can each be affixed in the adapter housing a first fastening means without requiring tools.

It is highly advantageous that the adapter housing is designed in one piece because it then oscillates more uniformly and thus has less influence on the measurement result. The tool-free fixation of the adapters in the adapter housing is also advantageous because this makes it possible to prevent overtightening of the fastening means and subsequent possible damage to or destruction of the measurement cell. The user friendliness is also increased by adapters that are used separately, thus facilitating a replacement of adapters.

The adapter housing preferably consists of a material which has a low thermal expansion and a high strength in particular at high temperatures, preferably above approximately 70° C., so that the adapter housing has the least possible influence on the oscillating measurement. The thermal insulation of the measurement cell from the outside is greatly improved by the inventive adapter housing because the adapter housing has an insulating effect and minimizes heat exchange with the environment. Furthermore, adjustment of the measurement temperature is greatly facilitated because the inventive adapter housing minimizes the heat flow to the outside. A material comprising a mixture of carbon and polyether ketone has been found to be especially suitable. Other materials that may be used include plastics having a low creep behavior even at elevated temperatures, for example, filled thermoplastics or thermosetting plastics. In addition, an adapter housing made of such a material is characterized by its low inherent weight, so the attenuation and thus also the measurement result are improved.

The adapters are preferably made of a chemically stable material which is resistant to the substances and cleaning agents that are used while also being transparent or at least semitransparent, so that impurities and deposits are rapidly and easily discernible visually by the user. Suitable materials include, for example, polymers such as FEP (perfluoroethylene propylene) and related polymers.

The adapter housing serves as a receptacle for the adapters and is connected to the housing of the measurement instrument. The adapter housing may be connected to the housing by a screw connection, a plug connection or an adhesive bond, wherein the connection or bond should be selected so that it is not loosened even with oscillation of the measurement cell and does not influence the measurement.

For detection of possible damage to or leakage of the measurement cell, the adapter housing further comprises a drain channel, so that fluid escaping from a damaged measurement cell is guided out of the housing and damage is immediately discernible by the user. Damage to the measurement cell is easily ascertained and the cell can be replaced quickly.

The measurement instrument for density determination further comprises a temperature regulating unit for regulating the temperature of the measurement cell, which is part of the control and/or regulating unit. The control and/or regulating unit may be arranged in the housing or may be designed as an external unit.

The measurement instrument further comprises means for inducing oscillation of the measurement cell, such that the adapters and the adapter housing are designed so that they do not interfere with the oscillation of the measurement cell.

BRIEF DESCRIPTION OF THE DRAWINGS

An inventive measurement instrument for density determination with an adapter housing is described below with reference to the figures, where the same elements are characterized with the same reference numerals and wherein.

DETAILED DESCRIPTION OF A PREFERRED EMBODIMENT

Figure 1:
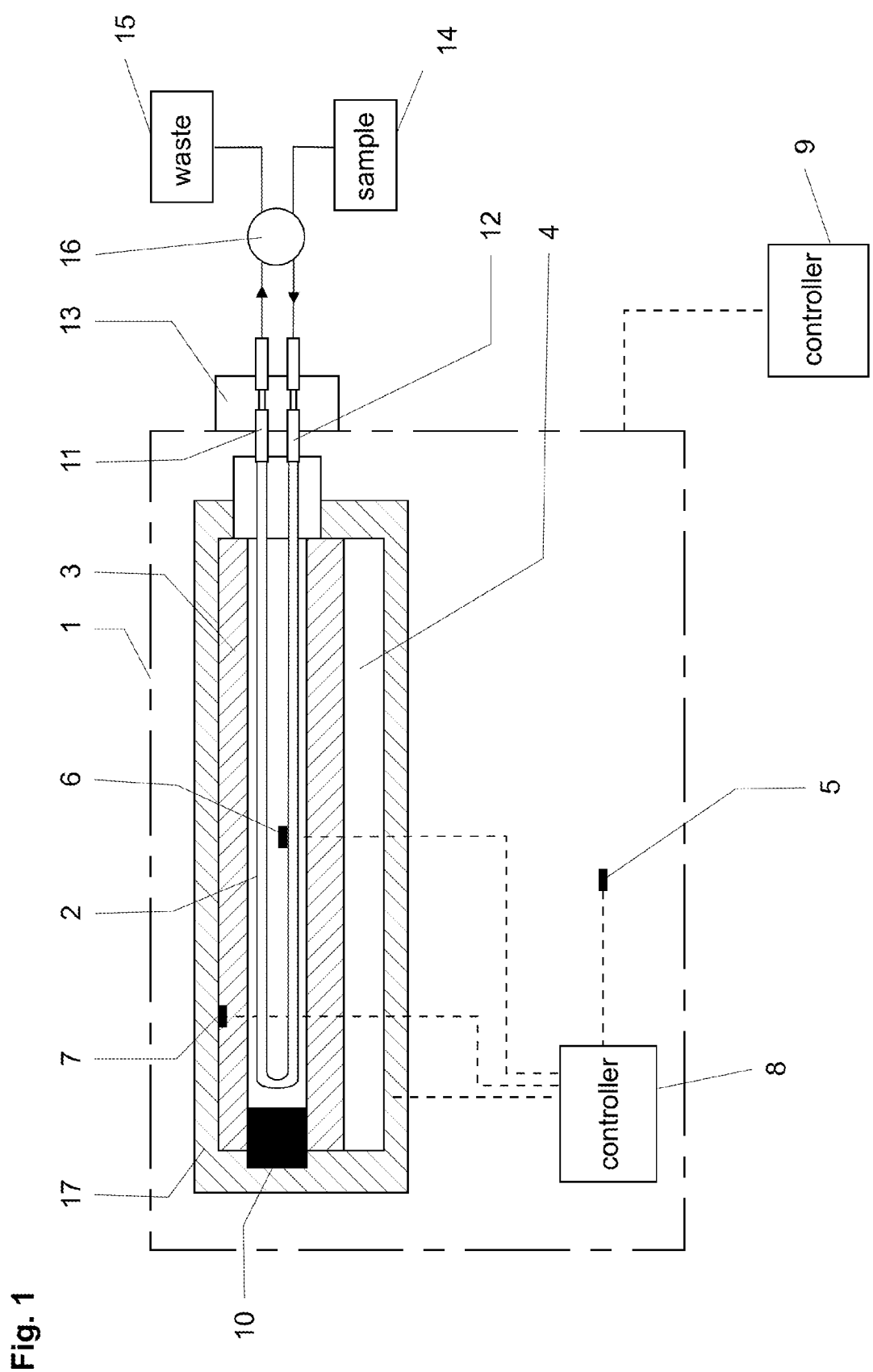
FIG. 1 is a schematic diagram of a measurement instrument for density determination.

FIG. 1 shows a schematic diagram of a density measurement instrument which operates according to the principle of a flexural resonator. The measurement instrument has a housing 1, which is merely indicated here and in which a measurement cell 2 is arranged. The measurement cell 2 is essentially a U-shaped tube, for example, a glass tube arranged in the housing 1 so that it is capable of oscillation.

The measurement cell 2 is surrounded by a thermally conducting area 3 to which a temperature regulating unit 4 in the form of Peltier elements is adjacent on at least one side. The temperature of the measurement cell 2 may be regulated by means of the temperature regulating unit 4. To detect and regulate the temperature, the measurement instrument comprises a plurality of temperature sensors 5, 6, 7, which are arranged in various locations in the housing 1. The temperature regulating unit 4 is connected to a control and/or regulating unit 8, 9, which may be arranged in and/or outside of the housing 1, as shown here. The measurement cell 2, the thermally conducting area 3 and the Peltier elements 4 are surrounded by thermal insulation 17.

To induce oscillation of the measurement cell 2, the measurement instrument comprises an oscillation unit 10, which is arranged on the closed end of the U-shaped measurement cell 2.

The measurement cell 2 may be filled or emptied through both of its open ends. Therefore, each end is connected to an adapter 11, 12, which is held by an adapter housing 13. The measurement cell 2 can be filled or emptied manually by means of a syringe through the adapters 11, 12. In addition, an adapter 11, 12 may be connected to a sample reservoir 14, and the other adapter may be connected to a waste container 15, and the measurement cell 2 may be operated with the help of a pump 16 in continuous flow.

Figure 2:
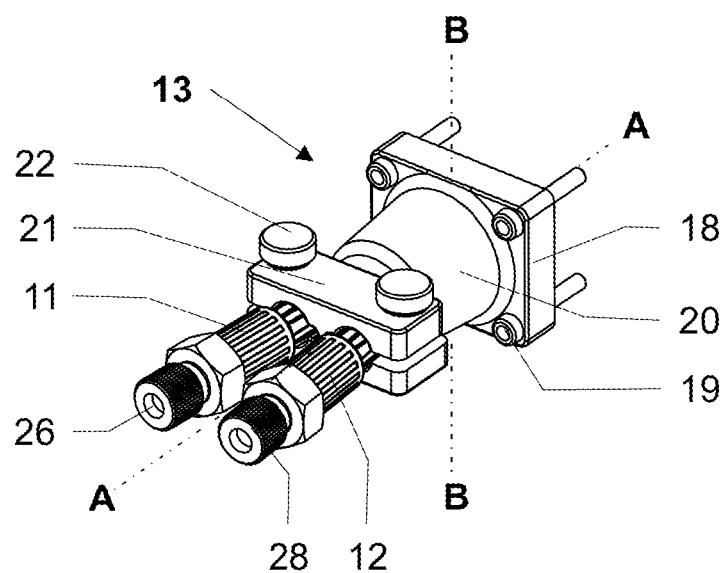
FIG. 2 is a three-dimensional diagram of an adapter housing having adapters inserted.

FIG. 2 shows the adapter housing 13 and the adapters 11, 12 in a three-dimensional diagram. The adapter housing 13 consists of a connection area 18, which serves to attach the adapter housing 13 to the housing of the measurement instrument. The connection area 18 may be attached to the housing with at least one fastening means 19, said fastening means 19 preferably being designed as a screw.

A bell-shaped transitional area 20 connecting the connection area 18 to a receptacle area 21 for the adapters 11, 12 is connected to the connection area 18. The connection area 18, the transitional area 20 and the receptacle area 21 are designed in one piece of a polymer material, for example, carbon-enriched polyether ketone. As shown clearly in FIGS. 3 through 5, the receptacle area 21 has two separate receptacles 23, 24 having clamping jaws for the adapters 11, 12, so that the latter can be replaced independently of one another. The adapters 11, 12 are each affixed in the receptacle using additional fastening means 22, for example, a pin or a screw. The fastening means 22 are selected, so that the adapters 11, 12 can be affixed manually and in particular without tools.

Figure 3:
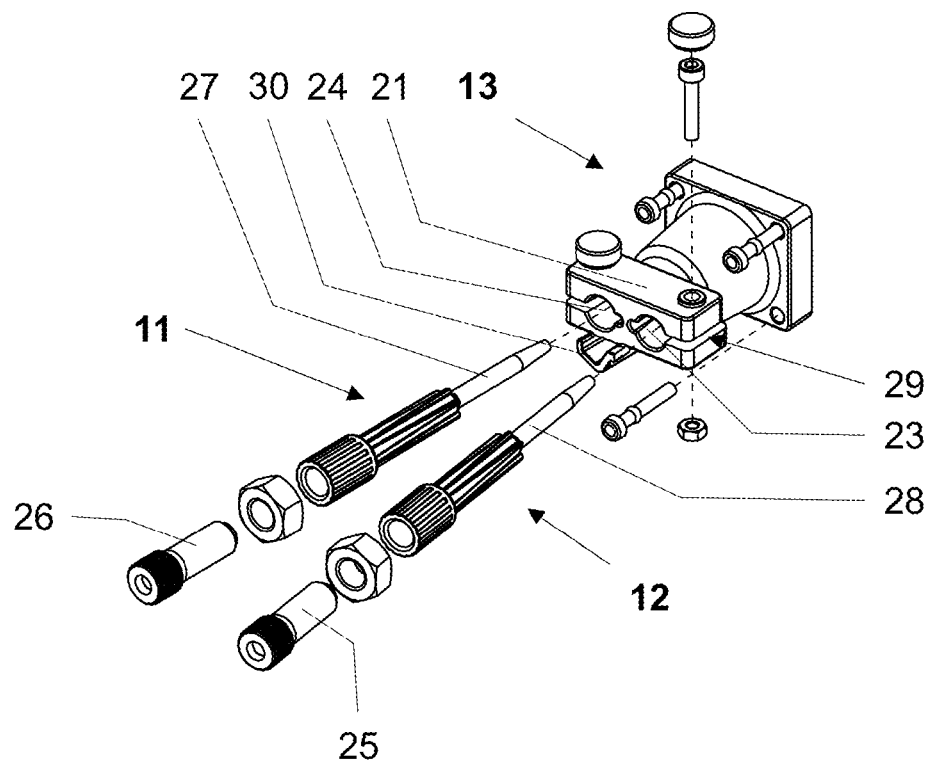
FIG. 3 is a three-dimensional exploded view of an adapter housing and the respective adapters.

FIG. 3 shows an exploded diagram of FIG. 2 where the receptacles 23, 24 can be seen in the adaptor housing 13, or more precisely its receptacle area 21. The receptacles 23, 24 have an essentially round diameter and a recess 29, which creates a connection to the outside, so that by compression by means of suitable fastening means 22 such as a screw, for example, the diameter of the receptacle 23, 24 can be reduced and a clamping jaw can be clamped securely like the respective adapters 11, 12.

In addition, the adapter housing 13 has a drain channel 30 through which the measurement medium can escape from the measurement instrument in the event of a damaged measurement cell. The drain channel 30 thus has means for detecting a leak and also serves to guide any measurement medium inadvertently escaping out of the measurement instrument.

Each adapter 11, 12 comprises a tube connection 25, 26 at one end and a connection 27, 28 for the measurement cell at the other end. The connections 27, 28 are designed to be essentially tapered to a point and adapted to the outputs of the measurements cells so that the adapters 11, 12 do not interfere with or prevent oscillation of the measurement cell. One tube connection 25, 26 is connected to each connection 27, 28 by means of a nut as shown here.

Instead of a tube connection 25, 26, the end may also be designed as a pipe connection or as connection for manual loading using a syringe.

Figure 4:
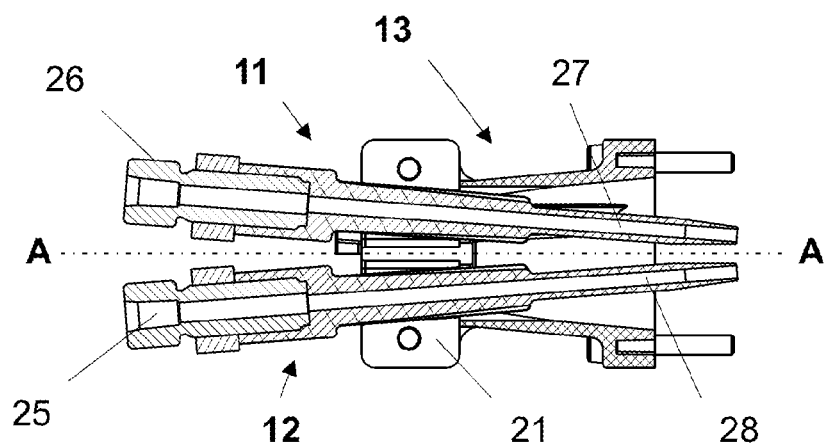
FIG. 4 is a section through the adapter housing along the plane A-A in FIG. 2 with the adapters inserted.

FIG. 4 shows a section through the assembled adapter housing 13 shown in FIG. 2 and the adapters 11, 12 along plane A-A. As shown here, the tube connections 25 to 26 are mostly guided in the connections 27, 28 and are affixed with a nut or some other suitable fastening means. The receptacles 23, 24 are arranged in such a way that the adapters 11, 12 are guided obliquely in the adapter housing, so that the free ends of the connections 27, 28 form an acute angle.

Figure 5:
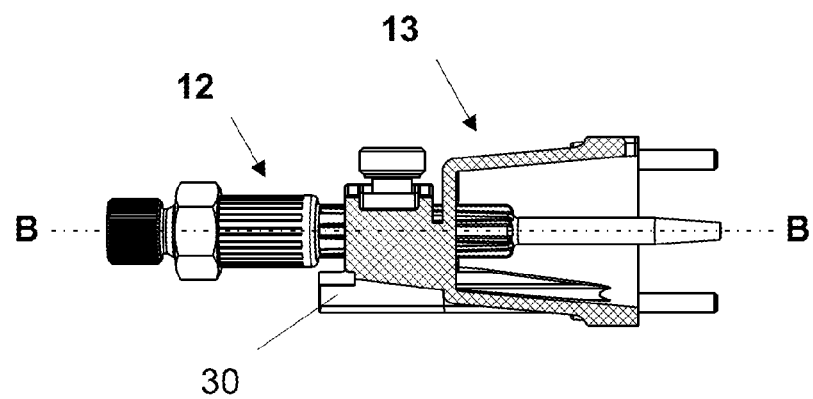
FIG. 5 is a section through the adapter housing along the plane B-B in FIG. 2 with the adapters inserted.

FIG. 5 shows a section through the assembled adapter housing 13 shown in FIG. 2 and the adapters 11, 12 along the plane B-B. In this view, the arrangement of the drain channel 30 in the adapter housing 13 can be seen in particular. The drain channel 30 is preferably a part of the adapter housing, which is designed in one piece and extends outward from the bell-shaped transitional area 20 in the direction of the receptacle area 21.

Although the invention has been described by presenting specific exemplary embodiments, it is obvious that numerous other embodiment variants may be created with a knowledge of the present invention, for example, by combining the features of the individual exemplary embodiments and/or exchanging individual function units of the exemplary embodiments.

What is claimed is:

1. An instrument for measuring density of a fluid sample, comprising:
   a measurement cell;
   a housing in which the measurement cell is arranged, the housing comprising an inlet opening and an outlet opening for the fluid sample;

a first adapter, tapered at a first end for insertion into the inlet opening and adapted at a second end for connection to a reservoir containing the fluid sample;

a second adapter, tapered at a first end for insertion into the outlet opening and adapted at a second end for connection to a waste container for the fluid sample; and an adapter housing, which is designed in one piece for attachment to the housing, the adapter housing having a receptacle area that comprises a first and a second receptacle providing a feed-through for each of the first and the second adapters, a split of the receptacle area through the receptacles allowing transverse compression of an intermediate portion of each adapter in its receptacle.

2. The density measurement instrument of claim 1, further comprising:
a screw connection that connects the adapter housing to the housing.

3. The density measurement instrument of claim 1, further comprising:
a drain channel in the adapter housing.

4. The density measurement instrument of claim 3, wherein:
the drain channel is positioned in the housing to drain from a bottom surface thereof.

5. The density measurement instrument of claim 1, wherein:
the adapter housing comprises a mixture of polyether ketone and carbon.

6. The density measurement instrument of claim 1, further comprising:
a unit for regulating the temperature of the measurement cell as part of a control and/or regulating unit.

7. The density measurement instrument of claim 6, wherein:
the control and/or regulating unit is arranged in the housing.

8. The density measurement instrument of claim 1; further comprising:
a unit for inducing oscillation of the measurement cell.

9. The density measurement instrument of claim 1, wherein:
the adapters are made of a material that is at least semitransparent, so that impurities of the fluid sample are visually discernible therethrough.

10. The density measurement instrument of claim 1, further comprising:
a plug connection that connects the adapter housing to the housing.

11. The density measurement instrument of claim 1, further comprising:
an adhesive bond that connects the adapter housing to the housing.

12. The density measurement instrument of claim 1, wherein:
the first and second receptacles guide the respective adapters obliquely in the adapter housing, so that the first ends thereof form an acute angle.

13. An instrument for measuring density of a fluid sample, comprising:
a measurement cell;
a housing in which the measurement cell is arranged, the housing comprising an inlet opening and an outlet opening for the fluid sample;
a first adapter, connecting the inlet opening to a reservoir containing the sample;
a second adapter, connecting the outlet opening to a waste container for the fluid sample, the first and second adapters comprising a material that is at least semitransparent, so that impurities of the fluid sample are visually discernible therethrough;
an adapter housing, designed in one piece of a mixture of polyether ketone and carbon, the adapter housing attached to the housing and comprising a feed-through for each of the first and the second adapters; and
means for compressively affixing the respective adapters in the adapter housing.

* * * * *